(12) United States Patent
Mowris et al.

(10) Patent No.: US 11,173,226 B1
(45) Date of Patent: Nov. 16, 2021

(54) BALANCED BIPOLAR IONIZER BASED ON UNBALANCED HIGH-VOLTAGE OUTPUT

(71) Applicants: Robert J. Mowris, Olympic Valley, CA (US); John Walsh, Bozeman, MT (US)

(72) Inventors: Robert J. Mowris, Olympic Valley, CA (US); John Walsh, Bozeman, MT (US)

( * ) Notice: Subject to any disclaimer, the term of this patent is extended or adjusted under 35 U.S.C. 154(b) by 0 days.

(21) Appl. No.: 17/244,389

(22) Filed: Apr. 29, 2021

(51) Int. Cl.
*A61L 9/22* (2006.01)
*F24F 8/30* (2021.01)
*B03C 3/41* (2006.01)

(52) U.S. Cl.
CPC .................. *A61L 9/22* (2013.01); *F24F 8/30* (2021.01); *A61L 2209/15* (2013.01); *A61L 2209/16* (2013.01)

(58) Field of Classification Search
CPC .......... A61L 9/22; A61L 2209/16; F24F 8/30; B03C 3/41
See application file for complete search history.

(56) References Cited

U.S. PATENT DOCUMENTS

| | | | |
|---|---|---|---|
| 4,729,057 A * | 3/1988 | Halleck | H05F 3/04 361/213 |
| 5,055,963 A | 10/1991 | Partridge | |
| 6,118,645 A | 9/2000 | Partridge | |
| 6,515,458 B1 | 2/2003 | Partridge | |
| 6,693,788 B1 | 2/2004 | Partridge | |
| 7,120,006 B2 | 10/2006 | Sekoguchi | |
| 7,177,133 B2 | 2/2007 | Riskin | |
| 7,254,006 B2 | 8/2007 | Sekoguchi | |
| 7,256,979 B2 | 8/2007 | Sekoguchi | |
| 7,312,973 B2 | 12/2007 | Sekoguchi | |
| 7,961,451 B2 | 6/2011 | Sekoguchi | |
| 8,009,405 B2 | 8/2011 | Gefter | |
| 8,106,367 B2 | 1/2012 | Riskin | |
| 8,576,535 B2 | 11/2013 | Sekoguchi | |
| 8,611,065 B2 | 12/2013 | Riskin | |
| 8,624,476 B2 | 1/2014 | Sekoguchi | |
| 8,710,456 B2 | 4/2014 | Klochkov | |
| 8,773,837 B2 | 7/2014 | Partridge | |
| 8,773,838 B2 | 7/2014 | Takeda | |

(Continued)

*Primary Examiner* — Kevin Joyner
(74) *Attorney, Agent, or Firm* — Averill & Green; Kenneth L. Green

(57) ABSTRACT

A balanced bipolar ionizer that generates zero or nearly-zero ozone concentration by providing a bipolar ion concentration ratio greater than 80 percent based on a high-voltage output ratio less than 80 percent over a range of electric signal inputs. A signal-conditioning element provides an excitation signal to a step-up transformer which provides an output voltage to a positive and a negative voltage multiplier which provide a positive high-voltage output greater than an absolute value of a negative high-voltage output or vice versa. The high-voltage output ratio is equal to a minimum of an absolute value of a negative and positive high-voltage output divided by a maximum of the absolute value of the negative and positive high-voltage output. The bipolar ion-concentration ratio is equal to a minimum of an absolute value of a negative-ion and positive-ion concentration divided by a maximum of the absolute value of the negative-ion and positive-ion concentration.

24 Claims, 9 Drawing Sheets

(56) References Cited

U.S. PATENT DOCUMENTS

| | | |
|---|---|---|
| 8,861,167 B2 | 10/2014 | Waddell |
| 9,142,378 B2 | 9/2015 | Sekoguchi |
| 9,421,291 B2 | 8/2016 | Robert |
| 9,510,431 B2 | 11/2016 | Oldynski |
| 9,843,169 B2 | 12/2017 | Riskin |
| 9,918,374 B2 | 3/2018 | Oldynski |
| 9,922,792 B2 | 3/2018 | Nishida |
| 9,985,420 B2 | 5/2018 | Sekoguchi |
| 10,073,055 B2 | 9/2018 | Waddell |
| 10,109,449 B2 | 10/2018 | Ezaki |
| 10,128,075 B2 | 11/2018 | Waddell |
| 10,317,096 B2 | 6/2019 | Waddell |
| 10,319,569 B2 | 6/2019 | Waddell |
| 10,322,205 B2 | 6/2019 | Waddell |
| 10,383,970 B2 | 8/2019 | Waddell |
| 10,566,769 B2 | 2/2020 | Waddell |
| 10,695,455 B2 | 6/2020 | Waddell |
| 10,710,123 B2 | 7/2020 | Waddell |
| 10,737,279 B2 | 8/2020 | Gefter |
| 10,786,818 B2 | 9/2020 | Galbreath |
| 10,910,186 B2 | 2/2021 | Nishida |
| 2007/0103842 A1 | 5/2007 | Partridge |
| 2010/0014635 A1 | 2/2010 | Vaynerman |
| 2015/0059580 A1* | 3/2015 | Clement .................. B03C 3/49 96/18 |
| 2016/0167059 A1 | 6/2016 | Waddell |
| 2016/0367712 A1* | 12/2016 | Robert ..................... A61L 9/22 |
| 2019/0247893 A1 | 8/2019 | Waddell |
| 2020/0161839 A1 | 5/2020 | Waddell |
| 2020/0179557 A1 | 6/2020 | Waddell |
| 2020/0340679 A1 | 10/2020 | Waddell |
| 2020/0388994 A1 | 12/2020 | Waddell |

\* cited by examiner

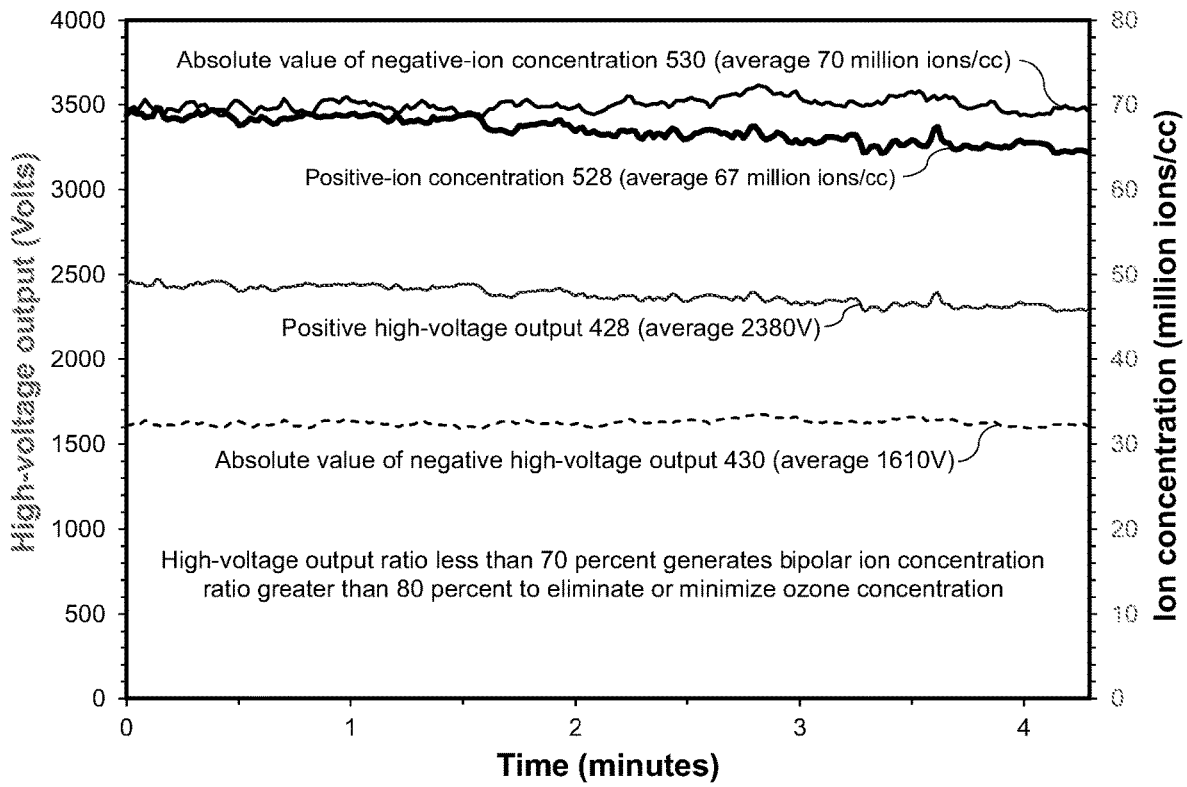

FIG. 8

| | High-voltage output ratio < 80% and bipolar ion concentration ratio > 80% | | | | | | | |
|---|---|---|---|---|---|---|---|---|
| # | Input voltage VAC | Positive high-voltage output (VDC) | Absolute value of negative high-voltage output (VDC) | High-voltage output ratio | Positive-ion concentration (million ions/cc) | Absolute value of negative-ion concentration (million ions/cc) | Bipolar ion concentration ratio | Ozone (ppm) |
| 1 | 20 | 1970 | 1320 | 67% | 54 | 63 | 86% | < 0.05 |
| 2 | 24 | 2380 | 1610 | 68% | 67 | 70 | 96% | < 0.05 |
| 3 | 29.3 | 2970 | 2020 | 68% | 72 | 78 | 92% | < 0.05 |
| 4 | 20 | 1430 | 2150 | 67% | 53 | 63 | 84% | < 0.05 |
| 5 | 24 | 1720 | 2530 | 68% | 65 | 76 | 86% | < 0.05 |
| 6 | 29.2 | 2050 | 3180 | 64% | 70 | 83 | 84% | < 0.05 |

FIG. 9

| Known prior art high-voltage output ≥ 90% and bipolar ion concentration ratio ≤ 80% | | | | | | | | |
|---|---|---|---|---|---|---|---|---|
| # | Input voltage VAC | Positive high-voltage output (VDC) | Absolute value of negative high-voltage output (VDC) | High-voltage output ratio | Positive-ion concentration (million ions/cc) | Absolute value of negative-ion concentration (million ions/cc) | Bipolar ion concentration ratio | Ozone (ppm) |
| 7 | 20 | 1407 | 1408 | 100% | 59 | 39 | 66% | 0.08 |
| 8 | 24 | 1413 | 1431 | 99% | 65 | 46 | 71% | 0.12 |
| 9 | 29.3 | 1433 | 1600 | 90% | 71 | 55 | 77% | 0.27 |

BALANCED BIPOLAR IONIZER BASED ON UNBALANCED HIGH-VOLTAGE OUTPUT

TECHNICAL FIELD

This invention relates generally to the field of air treatment, and more particularly to apparatus and methods for a bipolar ionizer. Examples include applications to improve indoor air quality in buildings, automobiles, airplanes, trains, boats, transportation systems, or enclosed environments with Heating, Ventilating, Air Conditioning (HVAC) systems.

BACKGROUND OF THE INVENTION

Known bipolar ionizers are generally installed at an inlet of a fan installed on a Heating, Ventilating, Air Conditioning (HVAC) system. Bipolar ionizers may also be installed on a fan motor or a fan blade or inside an air duct or on the inlet of a fan of an air cleaner. Known bipolar ionizers are used to produce high concentrations of positive and negative ions which attach to particles in a volume of air or particles in an airflow volume causing said particles to become positively or negatively charged and combine with other particles which become larger and heavier. Clusters of larger and heavier particles are removed from the air by air filters or removed from the air by being attracted to surfaces in a duct system or a surfaces inside a building. Bipolar ions are also attracted to virus, bacteria, mold, and other airborne pathogenic microbes. When positive and negative ions combine on the surface of a pathogen, a chemical reaction occurs on the cell surface membrane which produces hydroxide (OH+ or OH−) radicals which removes a hydrogen atom (H) from the pathogen. This chemical reaction severs a protein on the cell membrane which deactivates or destroys the pathogen. The ionized OH radicals bond with the removed hydrogen and form water vapor (H2O). Bipolar ionization kills pathogens without damaging the DNA in the interior cells of the pathogen, so it does not cause cancer. Bipolar ionization also breaks down hydrocarbon chains in harmful Volatile Organic Compounds (VOCs) into harmless compounds such as oxygen, nitrogen, water vapor, and carbon dioxide. Bipolar ionization also removes dust and odors.

The California Air Resources Board (CARB) adopted a regulation to limit ozone emissions from indoor air cleaning devices (AB 2276). Since 2010, all indoor air cleaners sold in, or shipped to, California must meet ozone emission and electrical safety standards and produce an emission concentration less than 0.050 parts per million (ppm) of ozone for 8 to 24 hours. https://ww2.arb.ca.gov/sites/default/files/2017-08/acrfactsheet.pdf https://ww2.arb.ca.gov/sites/default/files/2020-03/air-cleaner-regulation.pdf https://ww2.arb.ca.gov/resources/fact-sheets/californias-regulation-limit-ozone-emissions-indoor-air-cleaning-devices. The United States (US) Food and Drug Administration (FDA) requires ozone output of indoor medical devices to be no more than 0.05 ppm. See https://www.accessdata.fda.gov/scripts/cdrh/cfdocs/cfcfr/CFRSearch.cfm?fr=801.415. The US Occupational Safety and Health Administration (OSHA) requires that workers not be exposed to an average concentration of more than 0.10 ppm for 8 hours. The US Environmental Protection Agency (EPA) ozone standard is a maximum 8 hour average concentration of 0.08 ppm. See https://www.epa.gov/indoor-air-quality-iaq/ozone-generators-are-sold-air-cleaners#ozone-health.

Known bipolar ionizers may operate over a range of electrical signal inputs from 20 Volts Alternating Current (VAC) to 30 VAC or line voltages from 120 to 277 VAC. Bipolar ionizers for HVAC systems are typically designed to operate at 24 VAC, but HVAC system transformer voltages may vary from 24 to 30 VAC. Known bipolar ionizers operating at transformer voltages from 24 to 30 VAC may provide higher ozone concentrations than allowed by the CARB and US FDA. The Underwriters Laboratories (UL) 867 Section 40 ozone concentration tests or the Canadian Standards Association (CSA) 22.2 Number 187 in-duct ozone concentration tests are used to certify polar and bipolar ionizers for public safety. These tests might provide false positive results if tests are only performed at a single transformer voltage of 24 VAC.

Field tests indicate that some bipolar ionizers are sensitive to magnetic fields from rare earth magnets used to attach bipolar ionizers to sheet metal surfaces of HVAC ducts or fan housings. A bipolar ionizer with two rare earth magnets installed by the Original Equipment Manufacturer (OEM) caused ion concentrations to be reduced from 50 to 100 million ions per cubic centimeter (ions/cc) to 50 to 100 ions/cc. Lower ion concentrations reduces the efficacy of bipolar ionizers to remove particles, break down VOCs, and inactivate airborne pathogens.

Known prior art bipolar ionizers only have one electrical signal input (and a common signal input) which typically requires the ionizer to be energized continuously which will cause dust to accumulate on the electrodes when the fan is turned off. Dust accumulation may require maintenance. Operating a fan continuously to power the ionizer continuously will significantly increase the fan energy use.

According to the National Institute of Standards and Technology (NIST) gas phase ion energetics data, the ozone gas ionization energy is 12.53±0.08 electron Volts (eV). See https://webbook.nist.gov/cgi/cbook.cgi?ID=C10028156&Mask=20#Ion-Energetics. The threshold high-voltage output is dependent on and may vary based on an ambient air temperature and a relative humidity as well as a distance the positive-ion electrode is from a grounded surface and the distance the positive-ion electrode is from the negative-ion electrode.

BRIEF SUMMARY OF THE INVENTION

A balanced bipolar ionizer that generates zero or nearly-zero ozone concentrations by providing a bipolar ion concentration ratio greater than 80 percent based on a high-voltage output ratio less than 80 percent over a range of electric signal inputs. The balanced bipolar ionizer provides ozone concentrations significantly less than the California Air Resources Board (CARB) and United States (US) Food and Drug Administration (FDA) ozone exposure limit of 0.05 parts per million (ppm) for 8 to 24 hours. Some known prior art bipolar ionizers provide ozone concentrations greater than the CARB ozone exposure limit of 0.05 ppm for 8 to 24 hours due to providing high-voltage output ratios greater than or equal to 90 percent and bipolar ion concentration ratios less than or equal to 80 percent. The present invention provides a solution to this unresolved problem by providing consistent ozone concentrations significantly less than the CARB and US FDA ozone exposure limit of 0.050 ppm or fifty (50) parts per billion (ppb) across a range of transformer voltages from 20 to 30 VAC and line voltages from 120 to 480 VAC.

The high-voltage output ratio is equal to a minimum of an absolute value of a negative high-voltage output and a positive high-voltage output divided by a maximum of the absolute value of the negative high-voltage output and the positive high-voltage output. The bipolar ion concentration ratio is equal to a minimum of an absolute value of a negative-ion concentration and a positive-ion concentration divided by a maximum of the absolute value of the negative-ion concentration and the positive-ion concentration.

The balanced bipolar ionizer comprises a signal conditioning element to process an electrical signal input and provide an excitation signal to a step-up transformer which provides an output voltage to a positive and negative voltage multiplier which provide a positive high-voltage output greater than an absolute value of a negative high-voltage output or vice versa to a positive-ion electrode and a negative-ion electrode. The electrical signal input may be 20 to 30 Volts Alternating Current (VAC) or a line voltage from 120 to 480 VAC. The signal conditioning element may comprise at least one: wire, opto-isolator, diode, Zener diode, resistor, capacitor, oscillator or microprocessor (OSC/uP), Field Effect Transistor (FET), input and/or output feedback circuit, Resistor Divider Network (RDN), operational amplifier (Op Amp), or comparator. The positive and negative voltage multipliers generate a Direct Current (DC) high-impedance high-voltage output to the positive or negative electrodes. The positive or negative multipliers are comprised of one or more voltage multiplier stages where each voltage multiplier stage is comprised of two capacitors and two diodes (e.g., "Cockroft-Walton" multiplier). The positive voltage multiplier may provide at least one more multiplier stage than the negative voltage multiplier or vice versa. One embodiment provides +2.5+/−0.6 kilo Volts (kV) on the positive- and −1.7 kV+/−0.4 kV on the negative-ion electrode or +1.7 kV+/−0.4 kV on the positive- and −2.5+/−0.6 kV on the negative-ion electrode.

Another embodiment of the balanced bipolar ionizer comprises an input voltage feedback circuit and a microprocessor that monitors a step-up transformer Direct Current (DC) input voltage and continuously adjusts a frequency and duty cycle of a digital signal to the FET to produce an excitation signal for the step-up transformer to produce an output voltage to the positive and negative voltage multipliers to create the positive and negative high-voltage outputs to the positive and negative-ion electrodes. A duty cycle is a fraction of a period when a signal is active. A period is the time it takes for a signal to complete one on-off cycle.

Another embodiment may include a high-voltage output feedback circuit, an active element, and a microprocessor to continuously adjust the frequency and duty cycle of the digital signal to the FET to produce the excitation signal for the step-up transformer to achieve the positive and negative high-voltage outputs to the positive and negative-ion electrodes.

The balanced bipolar ionizer is not be impacted by the position or polarity of rare earth magnets fastened to the surface of the bipolar ionizer to attach the bipolar ionizer to sheet metal used for the Heating, Ventilating, Air Conditioning (HVAC) duct work or blower fan housings. Another embodiment provides status or fault alarm information using a Light Emitting Diode (LED) or wireless communication. Another embodiment of the balanced bipolar ionizer may include at least one electrical signal input to energize the bipolar ionizer by more than one control signal to allow bipolar ionizer operation during a thermostat call for cooling or heating without operating a thermostat Fan G signal continuously. This embodiment will save HVAC energy.

BRIEF DESCRIPTION OF THE SEVERAL VIEWS OF THE DRAWINGS

The above and other aspects, features and advantages of the balanced bipolar ionizer with unbalanced high-voltage output will be more apparent from the following more particular description thereof, presented in conjunction with the following drawings.

FIG. 8 shows time series measurements of high-voltage output and the sampled bipolar ion concentration versus time for the balanced bipolar ionizer.

FIG. 9 provides test results for the balanced bipolar ionizer with high-voltage output less than 80 percent with produces zero or very low ozone concentrations.

FIG. 10 provides test results for a known prior art bipolar ionizer with high-voltage output greater than or equal to 90% which produces high ozone concentrations.

Corresponding reference characters indicate corresponding elements throughout the several views of the drawings.

DETAILED DESCRIPTION OF THE INVENTION

The following description of a bipolar ionizer with an unbalanced high-voltage output to provide a balanced and calibrated bipolar ion concentration is the best mode presently contemplated. This description is not to be taken in a limiting sense, but is made merely for the purpose of describing one or more preferred embodiments of the invention. The scope of the invention should be determined with reference to the claims.

Figure 1:
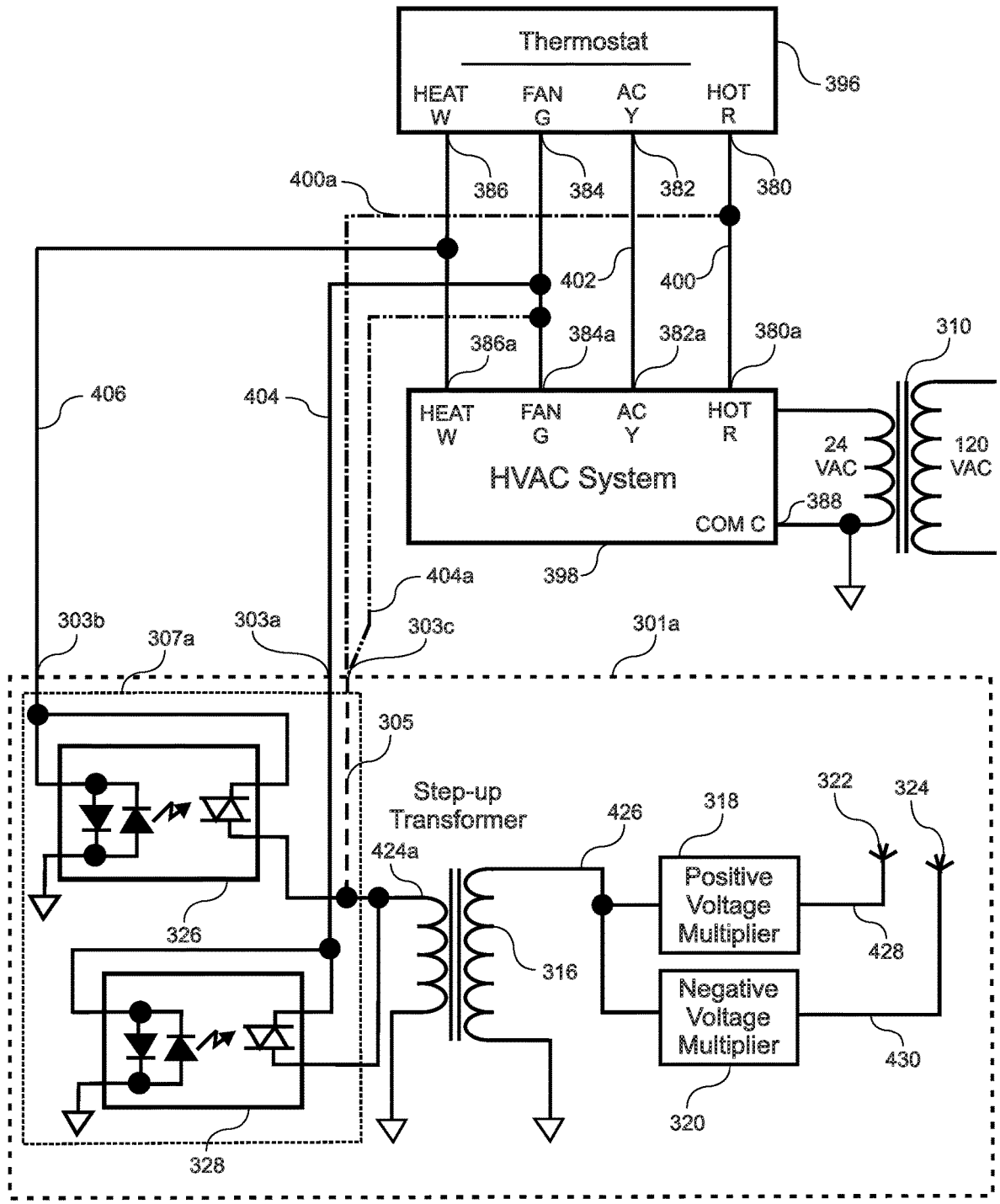
FIG. 1 shows a first embodiment of the balanced bipolar ionizer with a step-up transformer, positive/negative voltage multipliers, and a first signal conditioning element using a single wire for a first electrical signal input or two opto-isolators.

FIG. 1 shows a first embodiment of the balanced bipolar ionizer 301a (large dashed line) with a first signal conditioning element 307a (small dashed line), a step-up transformer 316, a positive voltage multiplier 318 connected to a positive-ion electrode 322, and a negative voltage multiplier 320 connected to a negative-ion electrode 324. The first signal conditioning element 307a comprises: 1) a first input terminal 303a connected to a first opto-isolator 328 connected to the step-up transformer 316, 2) a second input terminal 303b connected to a second opto-isolator 326 connected to the step-up transformer 316, and 3) an alternative third input terminal 303c connected to a wire 305 connected to the step-up transformer 316. The alternative third input terminal 303c is only used for a single input embodiment shown receiving a second fan G signal 404a (dash-dot-dot-dash line) or a second hot R signal 400a (dash-dot-dash line).

FIG. 1 shows a fan G signal 404 connected to the first input terminal 303a and a heat W signal 406 connected to the second input terminal 303b. The opto-isolators allow either the first electrical signal input or the second electrical signal input (e.g., fan G signal 404, heat W signal 406) to energize the balanced bipolar ionizer 301a without causing a short circuit if both signals are energized simultaneously. A low-voltage signal on any of the signal input terminals will produce an excitation signal 424a to the step-up transformer 316 to generate a step-up transformer output voltage 426. FIG. 1 shows the electrical connections from a thermostat 396 to the HVAC system 398 and a 120 Volts Alternating Current (VAC) to a low-voltage 24 VAC transformer (hereafter referred to as a 24 VAC transformer) 310. The thermostat 396 may include a hot R terminal 380, an Air Conditioning (AC) Y terminal (AC Y terminal 382), a fan G terminal 384, a heat W terminal 386, and a COM C terminal 408 (not shown). The HVAC system 398 may include a hot R terminal 380a, an AC Y terminal 382a, a fan G terminal 384a, a heat W terminal 386a, and a COM C terminal 388.

FIG. 1 shows the step-up transformer output voltage 426 from the step-up transformer 316 is conducted to a positive voltage multiplier 318 and a negative voltage multiplier 320. The positive voltage multiplier generates a Direct Current (DC) high-impedance Positive Highvoltage Output (PHO 428) on a positive-ion electrode 322. The negative voltage multiplier generates a DC high-impedance Negative Highvoltage Output (NHO 430) on a negative-ion electrode 324. The positive voltage multiplier 318 and the negative voltage multiplier 320 contain an unequal number of multiplier stages to produce a high-voltage output ratio less than 80 percent and a bipolar ion concentration ratio greater than 80 percent. The high-voltage output ratio is equal to a minimum of an absolute value of a negative high-voltage output and a positive high-voltage output, divided by a maximum of the absolute value of the negative high-voltage output and the positive high-voltage output. The bipolar ion concentration ratio is equal to a minimum of an absolute value of a negative-ion concentration and a positive-ion concentration, divided by a maximum of the absolute value of the negative-ion concentration and the positive-ion concentration. The high-voltage output ratio is calculated using Equation 1.

$$HOR=[MIN(ABS(NHO),PHO)]/[MAX(ABS(NHO),PHO)] \quad \text{Eq. 1}$$

Where, HOR=high-voltage output ratio (fraction),
MIN=Minimum value,
ABS=absolute value,
MAX=Maximum value,
PHO=positive high-voltage output or PHO 428 (Volts), and
NHO=negative high-voltage output of NHO 430 (Volts).

Figure 2:
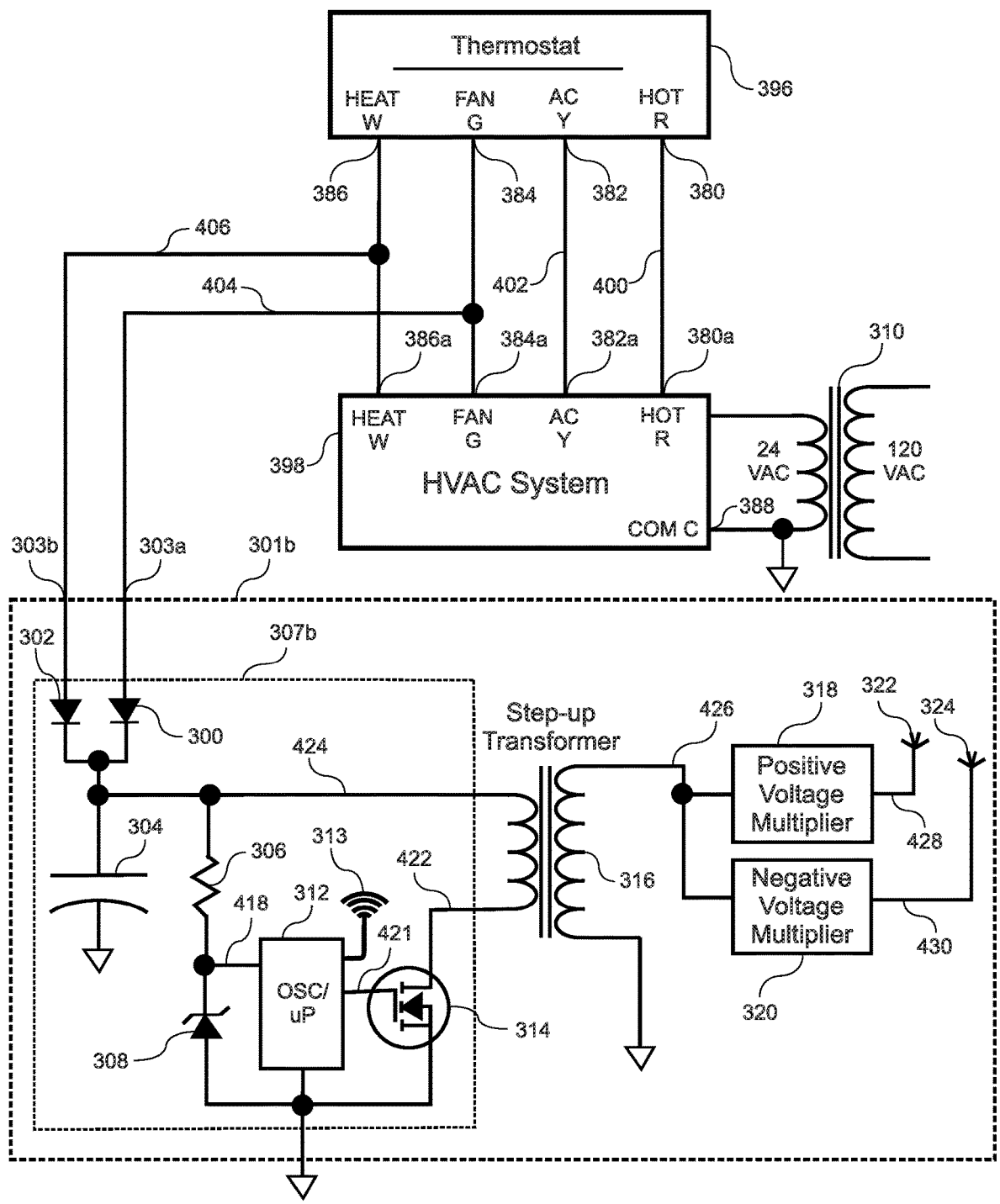
FIG. 2 shows a second embodiment with two input terminals, two diodes, a capacitor, a resistor, a Zener diode, a oscillator/microprocessor, and a Field Effect Transistor (FET).

FIG. 2 shows second balanced bipolar ionizer 301b with a second signal conditioning element 307b, the step-up transformer 316, the positive voltage multiplier 318 connected to the positive-ion electrode 322, and the negative voltage multiplier 320 connected to the negative-ion electrode 324. The thermostat 396 and the HVAC system 398 have the same terminals and electrical signals shown in FIG. 1. The second signal conditioning element 307b comprises: 1) a first input terminal 303a and a second input terminal 303b, 2) signal input processing circuit (a first diode 300, a second diode 302, a first capacitor 304, a first resistor 306, a first Zener diode 308), 3) a OSC/uP 312 (preferably a microprocessor "uP" or an oscillator "OSC"), and a first Field Effect Transistor (FET) (first FET 314). If the oscillator is used, then the oscillator may include at least one resistor and at least one capacitor. The first diode 300 and the second diode 302 rectify low-voltage signals from the thermostat or 24 VAC transformer and pass a positively rectified signal to the first capacitor 304 which creates the step-up transformer DC input voltage 424 to the step-up transformer 316. The first resistor 306 limits the current from the step-up transformer DC input voltage 424 that feeds the first Zener diode 308 to create a +5 Volt signal 418 to the OSC/uP 312. The +5 Volt signal 418 may be created using other components or methods.

FIG. 2 shows the OSC/uP 312 drives the gate of the first FET 314 with a digital signal 421 which may be a 0 Volt signal or a +5 Volt signal that varies in frequency and duty cycle to create the excitation signal 422 to the step-up transformer 316. When the first FET 314 is driven with a positive digital signal, the first FET 314 is energized and draws current from the step-up transformer DC input voltage 424 through the step-up transformer 316 to create a magnetic field within the core of the step-up transformer 316. When the first FET 314 is driven with a zero digital signal, the first FET 314 is gated off and the magnetic field in the transformer collapses which generates the step-up transformer output voltage 426. The step-up transformer output voltage 426 is passed to the positive voltage multiplier 318 and the negative voltage multiplier 320 which contain an unequal number of multiplier stages to produce a high-voltage output ratio less than 80 percent and a bipolar ion concentration ratio greater than 80 percent.

Figure 3:
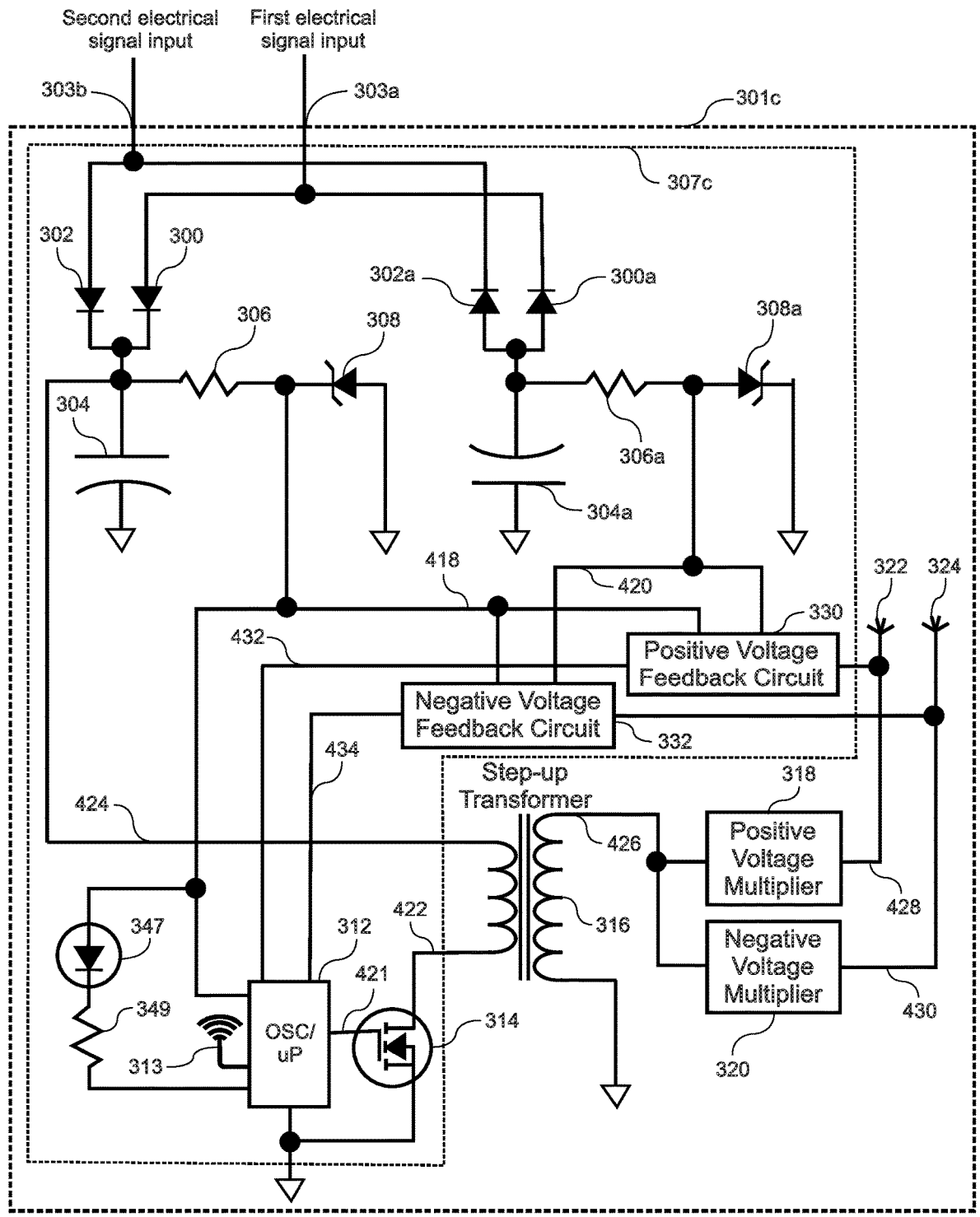
FIG. 3 shows a third embodiment of the balanced bipolar ionizer with a third signal conditioning element with a positive and a negative feedback circuit.

FIG. 3 shows a third balanced bipolar ionizer 301c with a third signal conditioning element 307c, the step-up transformer 316, the positive voltage multiplier 318 connected to the positive-ion electrode 322, and the negative voltage multiplier 320 connected to the negative-ion electrode 324. The third signal conditioning element 307c comprises: 1) a first input terminal 303a and a second input terminal 303b, 2) signal input processing circuit (a first diode 300, a second diode 302, a first capacitor 304, a first resistor 306, a first Zener diode 308, a third diode 300a, a fourth diode 302a, a second capacitor 304a, a second resistor 306a, a second Zener diode 308a), 3) a microprocessor (OSC/uP 312) and a first FET 314, and 4) a positive voltage feedback circuit 330 and a negative voltage feedback circuit 332. Also shown is a wireless antenna 313 to provide information regarding the status of the balanced bipolar ionizer. The wireless communication may use a WIFI (wireless fidelity), a Bluetooth (short-range wireless using UHF radio waves in the ISM bands, from 2.402 GHz to 2.480 GHz), or a LPWAN (Low-Power Wide-Area Network with data rates from 0.3 kbit/s to 50 kbit/s per channel) communication protocol. The positive and negative voltage feedback circuits allow the OSC/uP 312 to modulate the frequency and duty cycle of the step-up transformer output voltage 426 to achieve a consistent unbalanced high-voltage output ratio less than 80 percent and bipolar ion concentration ratio greater than 80 percent over a 20 to 30 VAC electrical signal input range.

FIG. 3 shows a first input terminal 303a connected to a first diode 300 and a third diode 300a and a second input terminal 303b connected to a second diode 302, and a fourth diode 302a. The first diode 300 is used to rectify a first electrical signal input (e.g., the fan G signal 404, the heat W signal 406, or the hot R signal), and pass the positively rectified signals to the first capacitor 304 which creates a DC voltage used as the step-up transformer DC input voltage 424. The first resistor 306 limits the current from the step-up transformer DC input voltage 424 to the first Zener diode 308 to create a +5 Volt signal 418 to the OSC/uP 312. The +5 volts signal 418 is also used by the positive voltage feedback circuit 330 and the negative voltage feedback circuit 332. The third diode 300a and the fourth diode 302a negatively rectify the first electrical signal input and the second electrical signal input and pass the negatively rectified signals to the second capacitor 304a which creates a negative DC voltage. The second resistor 306a limits the current from the second capacitor 304a to the second Zener diode 308a to create a −5 Volt signal 420 used by the positive voltage feedback circuit 330 and the negative voltage feedback circuit 332.

FIG. 3 shows the positive voltage feedback circuit 330 and the negative voltage feedback circuit 332 which contain at least one Resistor Divider Network (RDN) and one active element (not shown) to reduce the Positive High-voltage Output (PHO 428) and Negative High-voltage Output (NHO 430) to a Positive Low-voltage Feedback Signal (PLFS 432) and Negative Low-voltage Feedback Signal (NLFS 434). The PLFS 432 and the NLFS 434 are approximately 1000 times lower than the PHO 428 or NHO 430 output (1000:1). The at least one active element processes the PLFS 432 and NLFS 434 from the respective RDN. The active element may be selected from the group consisting of: 1) an operational amplifier (Op Amp) voltage follower (shown in FIG. 5); 2) a second FET voltage follower (shown in FIG. 6); and 3) a comparator (shown in FIG. 7). FIG. 3 shows a Light Emitting Diode (LED 347) which receives the +5 Volt signal 418. The LED 347 is connected to a LED resistor 349 which is connected to the OSC/uP 312. The LED 347 may provide status information or fault alarm messages.

Figure 4:
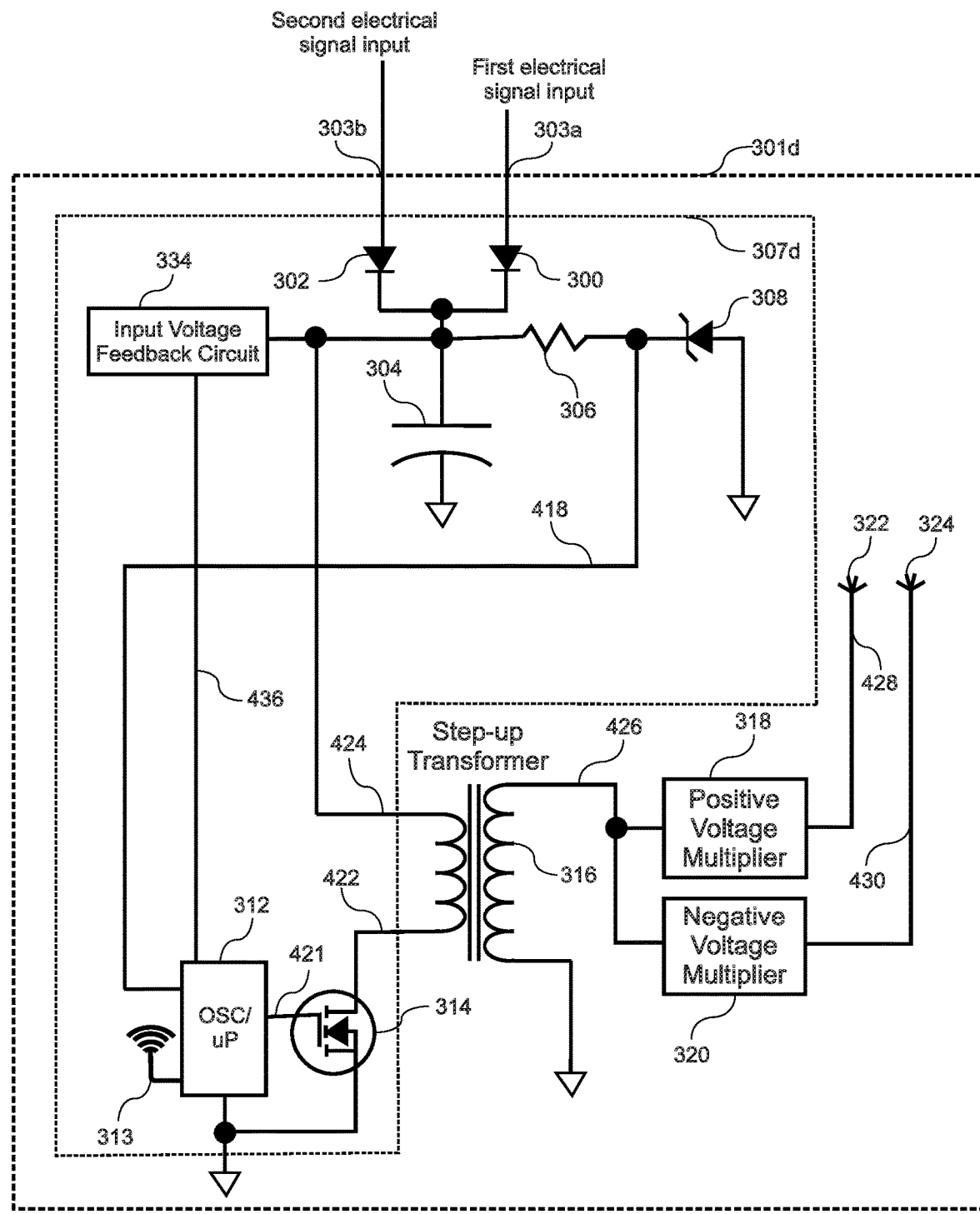
FIG. 4 shows a fourth embodiment of the balanced bipolar ionizer with a fourth signal conditioning element with an input voltage feedback circuit

FIG. 4 shows a fourth embodiment of the balanced bipolar ionizer 301d including: 1) a fourth signal conditioning element 307d with an input voltage feedback circuit 334, 2) a step-up transformer 316, 3) a positive voltage multiplier 318 connected to a positive-ion electrode 322, and 4) a negative voltage multiplier 320 connected to a negative-ion electrode 324. The fourth signal conditioning element 307d comprises: 1) a first input terminal 303a and a second input terminal 303b, and 2) signal input processing circuit (diodes, resistors, and capacitors), 3) an input voltage feedback circuit 334, and 3) a microprocessor (OSC/uP 312) and first FET 314. Similar to FIG. 2, the first diode 300, the second diode 302, the first capacitor 304, and the first Zener diode 308 are used to create the step-up transformer DC input voltage 424 and the +5 Volt signal 418 from a first or a second electrical signal input. A wireless antenna 313 may be used to provide information regarding the status of the balanced bipolar ionizer. As the electrical signal input varies from 20 VAC to 30 VAC, the OSC/uP 312 varies the frequency and duty cycle of the digital signal 421 to the first FET 314 and the excitation signal 422 to the step-up transformer 316 which varies the frequency and the duty cycle of the step-up transformer output voltage 426 to produce a high-voltage output ratio less than 80 percent for the PHO 428 and the NHO 430 and a bipolar ion concentration ratio greater than 80 percent from the positive-ion electrode 322 and the negative-ion electrode 324. The input voltage feedback circuit 334 includes a Resistor Divider Network (RDN) to reduce the step-up transformer DC input voltage 424 to an input voltage feedback signal 436 which varies between 0 and +5 VDC (Volts Direct Current) and is approximately 10 times lower than the step-up transformer DC input voltage 424. The input voltage feedback circuit 334 may be as simple as a low-resistance RDN to provide the input voltage feedback signal 436. Alternatively, the input voltage feedback circuit 334 shown in FIG. 4 may include a high-resistance RDN which contains at least one active element to process the voltage from the high-resistance RDN. The at least one active element may be selected from the group consisting of: an Operational Amplifier (Op Amp) shown in FIG. 5, a second FET shown in FIG. 6, and a feedback comparator shown in FIG. 7.

Figure 5:
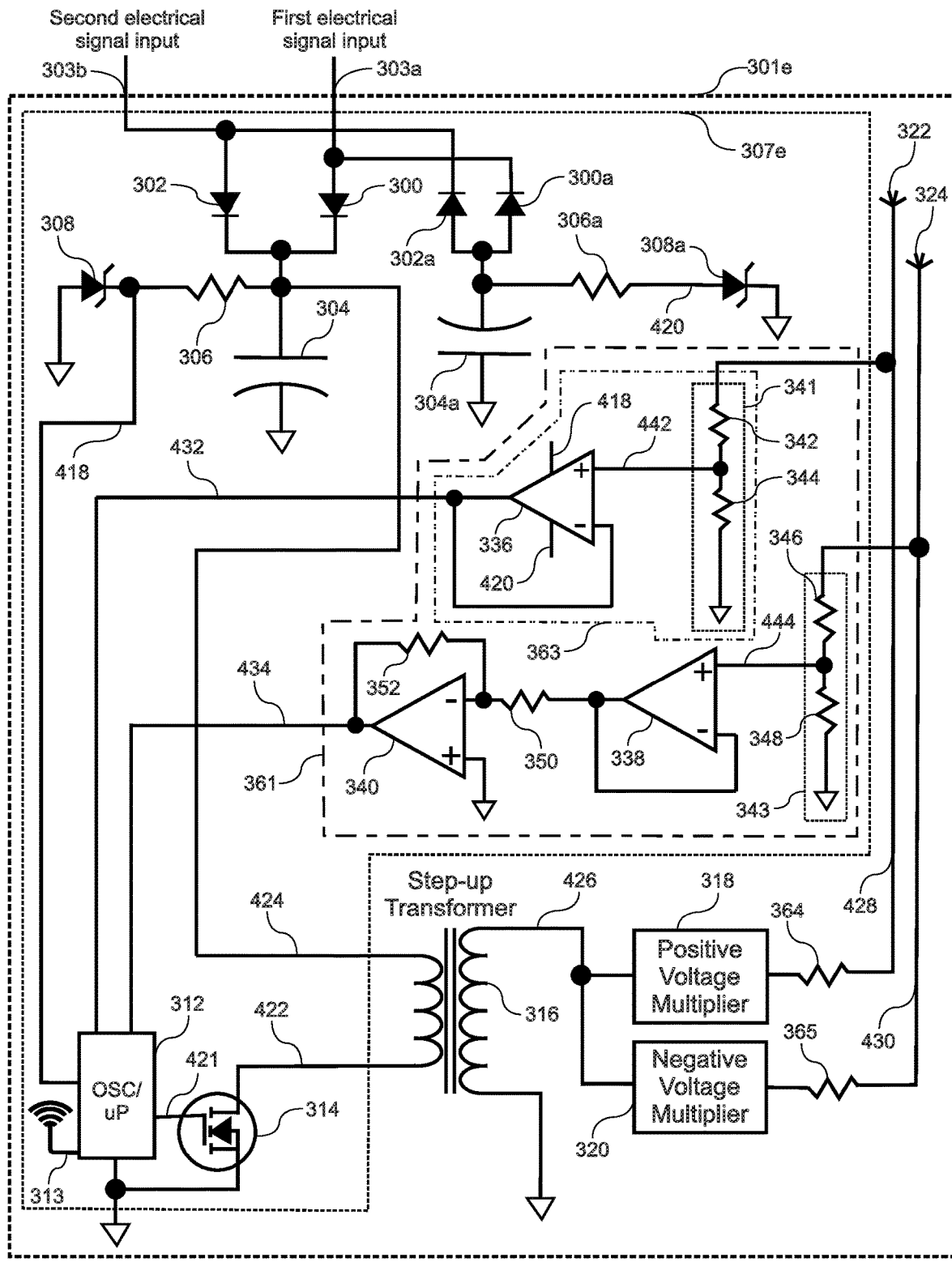
FIG. 5 shows a fifth embodiment of the balanced bipolar ionizer with a fifth signal conditioning element with an Operational Amplifier (Op Amp) feedback circuit.

FIG. 5 shows a fifth embodiment of the balanced bipolar ionizer 301e including: 1) a fifth signal conditioning element 307e, 2) a step-up transformer 316, 3) a positive voltage multiplier 318 connected to a Positive Electrode Resistor (PER 364) which is also connected to a positive-ion electrode 322, and 4) a negative voltage multiplier 320 connected to a Negative Electrode Resistor (NER 365) which is also connected to a negative-ion electrode 324. The PER 364 and the NER 365 are optionally installed as a safety measure to limit the instantaneous current carried by the positive- and the negative-ion electrodes. The fifth signal conditioning element 307e includes: 1) a first input terminal 303a and a second input terminal 303b, 2) a signal input processing circuit (diodes, resistors, and capacitors), 3) a microprocessor (OSC/uP 312) and a first FET 314, and 4) a feedback circuit 361. The positive voltage multiplier 318 creates the PHO 428 and the negative voltage multiplier 320 creates the NHO 430.

FIG. 5 shows the feedback circuit includes three operational amplifiers (Op Amps) and a positive Resistance Divider Network (positive RDN 341) and a negative RDN 343 to provide feedback from the PHO 428 and the NHO 430 for the microprocessor (OSC/uP 312) to modulate the frequency and duty cycle of a digital signal 421 to provide calibrated unbalanced high-voltage outputs to the positive/negative-ion electrodes (322 and 324). The positive RDN 341 is comprised of a positive feedback 100 MΩ resistor 342 a positive feedback 100 KΩ resistor 344 connected in series where 100 MΩ refers to 100 Million Ohms and 100 KΩ refers to 100 thousand Ohms. The positive RDN 341 reduces the PHO 428 by a ratio of 1000:1 to create a High-impedance Positive Voltage (HPV 442). The negative RDN 343 is comprised of a negative feedback 100 MΩ resistor 346 and a negative feedback 100 KΩ resistor 348 connected in series. The negative RDN 343 reduces the NHO 430 by a ratio of 1000:1 to create a High-impedance Negative Voltage (HNV 444). Similar to FIG. 3, a step-up transformer DC input voltage 424 and +5 Volt signal 418 are created from a first electrical signal input supplied to the first input terminal 303a or the second electrical signal supplied to the second input terminal 303b. The first Op Amp 336, the second Op Amp 338, and the third Op Amp 340 receive supply voltages from the +5 Volt signal 418 and the −5 Volt signal 420. The Op Amp is an integrated circuit with two inputs and one output to amplify a weak electrical signal or provide an output voltage difference between two inputs. A wireless antenna 313 may be used to provide status or fault alarm information regarding the balanced bipolar ionizer.

FIG. 5 shows the PLFS 432 is created by a first Op Amp 336 which follows the HPV 442 from the PHO 428. The output from the first Op Amp 336 creates the PLFS 432 sampled by the A/D converter of the OSC/uP 312. The first Op Amp 336 draws negligible current and provides a high-input impedance signal to the positive RDN 341 to not interfere with the accuracy of the signal. The second Op Amp 338 creates a low impedance negative voltage signal from the HNV 444 which is inverted to a positive voltage signal by the third Op Amp 340 in series with a first negative feedback 10 KÙ resistor 350 and a second negative feedback 10 KÙ resistor 352. The output from the third Op Amp 340 creates the NLFS 434 sampled by the A/D converter of the OSC/uP 312. Based on the PLFS 432 and/or the NLFS 434 the OSC/uP 312 varies the frequency and duty cycle of the digital signal 421 to the first FET 314 to produce a high-voltage output ratio less than 80 percent for the PHO 428 and the NHO 430 and a bipolar ion concentration ratio greater than 80 percent from the positive-ion electrode 322 and the negative-ion electrode 324.

FIG. 5 shows a Positive Electrode Resistor (PER 364) connected between the positive voltage multiplier 318 and the positive-ion electrode 322, and a Negative Electrode Resistor (NER 365) connected between the negative voltage multiplier 320 and the negative-ion electrode 324. The PER 364 and the NER 365 may be optionally installed as a safety measure to limit the instantaneous current carried by the positive- and the negative-ion electrodes. If the PER 364 or the NER 365 are installed, then these resistors may increase the high-voltage output ratio when the high-voltage output ratio is measured at the negative-ion electrode and the positive-ion electrode.

FIG. 5 shows the feedback circuit 361 is comprised of a High-voltage Measurement Circuit (HMC 363). The HMC 363 comprises the positive RDN 341 and the first Op Amp 336 which may be used to measure the high-voltage output ratio where the positive RDN 341 is connected to the emitting end of the positive-ion electrode 322 or the negative-ion electrode 324 and the output from the first Op Amp 336 is measured by a digital multimeter. The measured voltage will represent the high-voltage output divided by the positive RDN value (e.g., approximately 1001:1). If the positive RDN 341 is connected to the emitting end of the positive-ion electrode 322, the voltage from the first Op Amp 336 is a positive voltage output. If the positive RDN 341 is connected to the emitting end of the negative-ion electrode 324, then the voltage output from the first Op Amp 336 is a negative voltage. When measuring the emitting end of the positive-ion electrode 322 with the digital multimeter, the PER 364 would be connected in series with the positive RDN 341. Likewise the NER 365 would be in series when measuring the negative-ion electrode 324. This measurement method is used for data shown in FIG. 8, FIG. 9, and FIG. 10.

The PER 364 resistance reduces the measured voltage from the first Op Amp 336 by the ratio of the PER 364 (or the NER 365) and the positive feedback 100 MΩ resistor 342 plus the positive feedback 100 KΩ resistor 344 or the negative feedback 100 MΩ resistor 346 plus the negative feedback 100 KΩ resistor 348. The measured high-voltage output reduction fraction (Vrf) may be calculated using Equation 2.

$$Vrf = 1 - [PER\ 364\ or\ NER\ 365]/RDN1 \quad Eq.\ 2$$

Where, Vrf=high-voltage output reduction fraction with PER 364 or NER 365 (fraction),
PER 364=resistance of PER 364 (Ohms),
NER 365=resistance of NER 365 (Ohms), and
RDN1=a first RDN1 resistor comprised of a 100 MΩ plus 100 KΩ resistor or a second RDN2 comprised of a 200 MΩ plus 100 KΩ resistor.

For example, if the PER 364 value is 10 MΩ, then the high-voltage output reduction fraction from the first Op Amp 336 is approximately 90.01% of the actual output of the positive voltage multiplier 318. If unequal resistance values for the PER 364 and the NER 365 are used, a measurement of the emitting end of the positive-ion electrode 322 compared to the absolute value of a measurement of the emitting end of the negative-ion electrode 324 might produce similar or equal electrode voltages when the absolute value of the electrode voltages might actually be different by 30 to 40 percent. Unequal resistors might be installed between the voltage multipliers and the electrodes for safety or to make it difficult to measure the actual output of the voltage multipliers. The difference in the values of the unequal resistors would not impact the ion generation since the impedance of air is between 1.3 to 3.3 times 10^16 ohms (with ions present) and changes on the order of Mega Ohms (MΩs) between the unequal resistors would be insignificant with respect to the impedance of air (resistance of dry air is infinite with no ions present).

Figure 6:
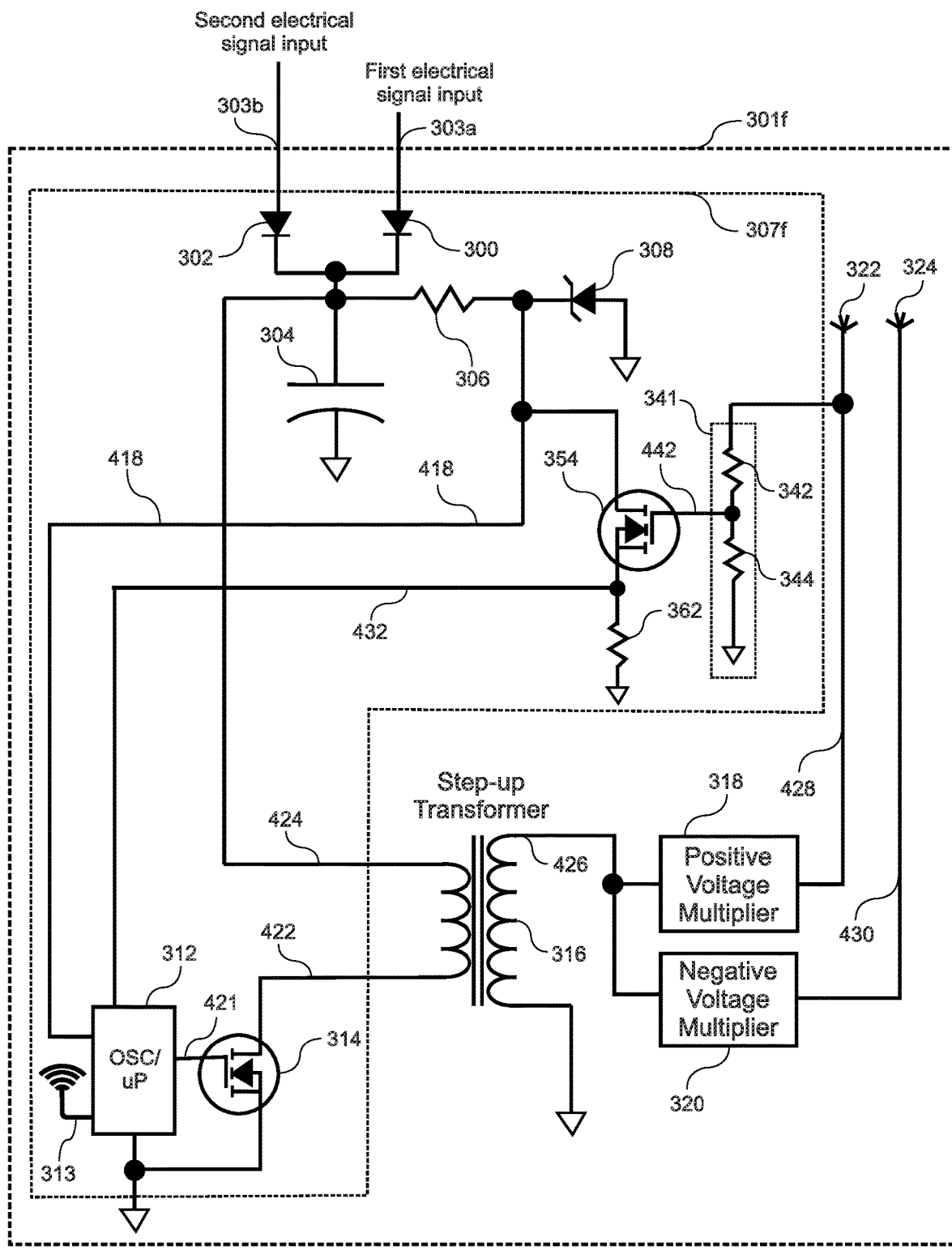
FIG. 6 shows a sixth embodiment of the balanced bipolar ionizer with a feedback circuit based on a Field Effect Transistor (FET) attached to the high-voltage output.

FIG. 6 shows a sixth embodiment of the balanced bipolar ionizer 301$f$ including: 1) a sixth signal conditioning element 307$f$, 2) a step-up transformer 316, 3) a positive voltage multiplier 318 connected to a positive-ion electrode 322, and 4) a negative voltage multiplier 320 connected to a negative-ion electrode 324. The sixth signal conditioning element 307$f$ comprises: 1) a first input terminal 303$a$ and a second input terminal 303$b$, 2) signal input processing circuit (a first diode 300, a second diode 302, a first capacitor 304, a first resistor 306, a first Zener diode 308), 3) a microprocessor (OSC/uP 312) and a first FET 314, and 4) a feedback circuit including a second FET 354 and a positive RDN 341. The feedback circuit provides feedback from the PHO 428 for the microprocessor (OSC/uP 312) to modulate a frequency and a duty cycle of a digital signal 421 to provide calibrated unbalanced high-voltage outputs to the positive-ion electrode 322 or the negative-ion electrode 324. A wireless antenna 313 may be used to provide occupants or maintenance personnel with information regarding the status of the balanced bipolar ionizer.

FIG. 6 shows the same signal input processing circuit shown in FIG. 2 to create the step-up transformer DC input voltage 424 and the +5 Volt signal 418 from an electrical power signal. Similar to FIG. 5, the positive RDN 341 is comprised of a positive feedback 100 MÙ resistor 342 and a positive feedback 100 KÙ resistor 344 connected in series. The positive RDN 341 reduces the PHO 428 by a ratio of 1000:1 to create the HPV 442. The output from positive RDN 341 is connected to the gate of the second FET 354. The second FET 354 is connected in a voltage follower configuration with the drain connected to the +5 Volt signal 418 and the source connected to a voltage follower load resistor 362. The output from the second FET 354 forms the PLFS 432 sampled by the A/D converter of the OSC/uP 312. Based on the PLFS 432, the OSC/uP 312 varies the frequency and duty cycle of the digital signal 421 to the first FET 314 to produce a high-voltage output ratio less than 80 percent for the PHO 428 and the NHO 430 to generate a bipolar ion concentration ratio greater than 80 percent from the positive-ion electrode 322 and the negative-ion electrode 324. The RDN and second FET 354 circuit may be duplicated to provide the OSC/uP 312 with the NLFS 434 from the NHO 430 (not shown).

Figure 7:
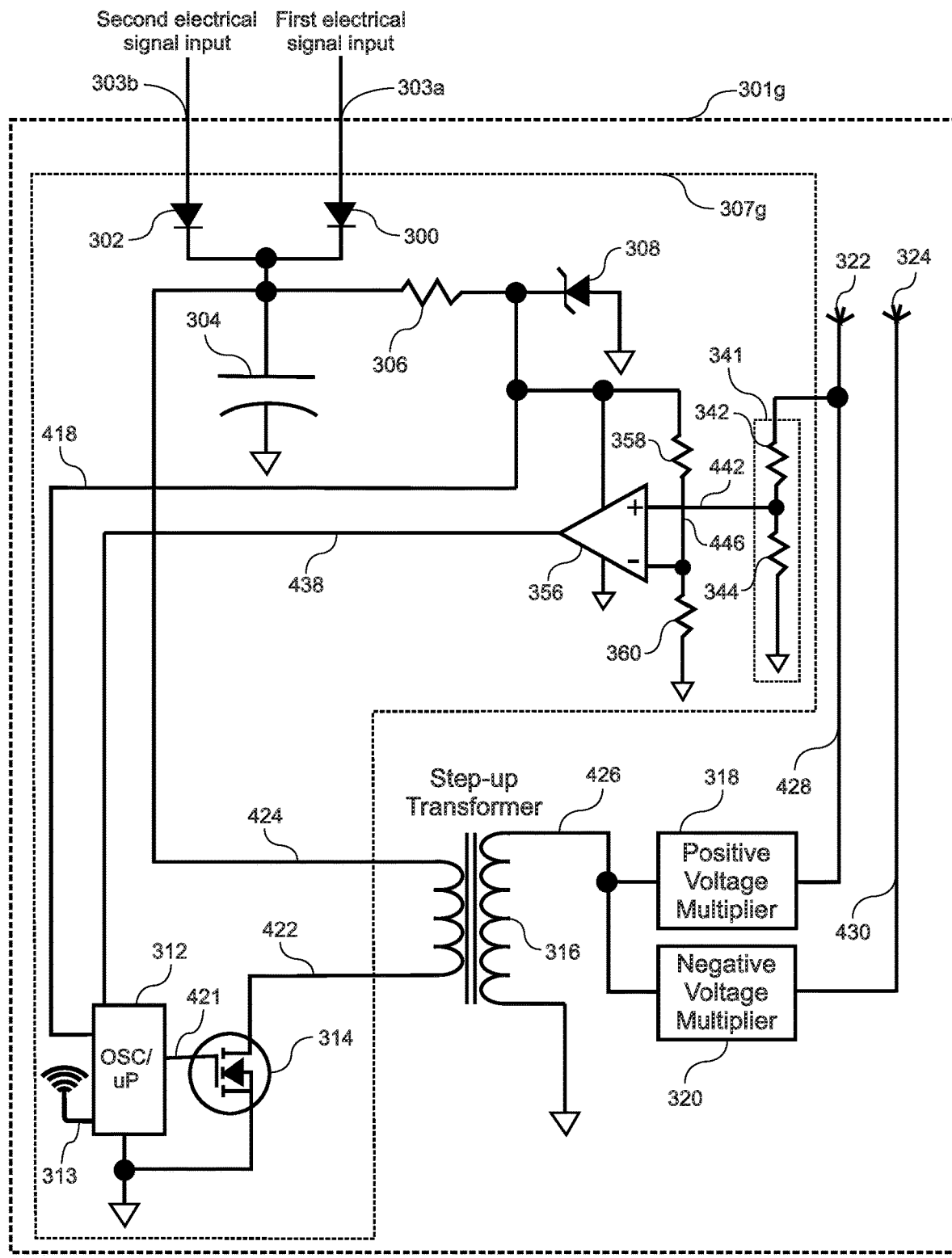
FIG. 7 shows a seventh embodiment of the balanced bipolar ionizer with a seventh signal conditioning element including a comparator feedback circuit.

FIG. 7 shows a seventh embodiment of the balanced bipolar ionizer 301$g$ including: 1) a seventh signal conditioning element 307$g$, 2) a step-up transformer 316, 3) a positive voltage multiplier 318 connected to a positive-ion electrode 322, and 4) a negative voltage multiplier 320 connected to a negative-ion electrode 324. The seventh signal conditioning element 307$g$ comprises: 1) a first input terminal 303$a$ and a second input terminal 303$b$, 2) signal input processing circuit (a first diode 300, a second diode 302, a first capacitor 304, a first resistor 306, a first Zener diode 308), 3) a microprocessor (OSC/uP 312) and a first FET 314, and 4) a feedback circuit including a positive feedback comparator 356 and a positive RDN 341. The feedback circuit is based on a comparator attached to the positive-ion electrode 322. A wireless antenna 313 may be used to provide information regarding the status of the balanced bipolar ionizer.

FIG. 7 shows the same signal input processing circuit shown in FIG. 2 to create the step-up transformer DC input voltage 424 and the +5 Volt signal 418 from an electrical power signal. Similar to FIG. 5, the RDN is comprised of a positive feedback 100 MÜ resistor 342 and a positive feedback 100 KÜ resistor 344 connected in series. The output from the positive RDN 341 is connected to the positive input of a positive feedback comparator 356. The negative input of the positive feedback comparator 356 is connected to a comparator reference voltage 446. The comparator reference voltage 446 is created by two resistors dividing the +5 Volt signal 418. A first positive reference resistor 358 is connected to the +5 Volt signal 418 and the negative terminal of positive feedback comparator 356. A second positive reference resistor 360 is connected to the negative terminal of positive feedback comparator 356 and ground. The comparator circuit may be connected to either the PHO 428 or the NHO 430. FIG. 7 only shows the PHO 428. The comparator circuit compares the output from the RDN to a reference voltage (e.g., 2.5 Volts Direct Current or DC) and provides the OSC/uP 312 with a Positive Comparator Feedback Signal (PCFS 438). The PCFS 438 is a digital 1 if the output from the RDN is greater than 2.5 VDC. The PCFS 438 is a digital 0 if the output from the RDN is less than 2.5 VDC. Based on the PCFS 438, the OSC/uP 312 varies the frequency and duty cycle of the digital signal 421 to the first FET 314 to produce a high-voltage output ratio less than 80 percent for the PHO 428 and the NHO 430 and a bipolar ion concentration ratio greater than 80 percent to maintain a comparator signal between 1 and 0. The comparator circuit may be duplicated to provide the OSC/uP 312 with a Negative Comparator Feedback Signal (NCFS 439) from the NHO 430 (not shown).

FIG. 8 shows time series measurements of the present invention bipolar ionizer with a high-voltage output ratio less than 80 percent to generate a bipolar ion concentration ratio greater than 80 percent to eliminate or minimize ozone concentration. The absolute value of the average negative high-voltage output (NHO 430) is 1610 Volts, and the average positive high-voltage output (PHO 428) is 2030 Volts. The absolute value of the average negative ion concentration 530 is 70 million ions per cubic centimeter (106/cc), and the average positive ion concentration 528 is 67 million ions/cc. The positive and negative ion concentrations are sampled using an ion counter that captures a fraction of the total positive and negative ion concentrations emitted from each electrode. The ion concentration ratios are more important than the magnitude of the ion concentrations. The high-voltage output ratio is 68 percent and the bipolar ion concentration ratio is 96 percent. The ozone concentration measured over 24 hours is zero parts per million (ppm) over a range of 20 to 29.3 VAC electrical signal inputs.

FIG. 9 provides test results of the balanced bipolar ionizer with a high-voltage output ratio less than 80 percent and bipolar ion concentration ratio greater than 80 percent. FIG. 9 provides tests of two embodiments: 1) a positive high-voltage output greater than the absolute value of the negative high-voltage output (rows 1-3); and 2) an absolute value of the negative high-voltage output greater than the positive high-voltage output (rows 4-6). The positive greater than negative high-voltage output tests in rows 1-3 at input voltages of 20 to 29.3 VAC provide zero parts per million (ppm) ozone concentrations over a 24-hour test period (<0.05 ppm). The high-voltage output ratio is 67 to 68% and the bipolar ion concentration ratio is 86 to 96%. The bipolar ion concentration ratio is equal to a minimum of an absolute value of a negative-ion concentration and a positive-ion concentration divided by a maximum of the absolute value of the negative-ion concentration and the positive-ion concentration. The high-voltage output ratio is equal to a minimum of an absolute value of a negative high-voltage output and a positive high-voltage output divided by a maximum of the absolute value of the negative high-voltage output and the positive high-voltage output.

FIG. 9 shows test data for the absolute value of the negative high-voltage output greater than the positive high-voltage output embodiment (rows 4-6). Tests were performed at input voltages ranging from 20 to 29.3 VAC with zero ozone ppm (<0.05 ppm) over a 24-hour test period. The high-voltage output ratio is less than 70-80 percent (i.e., 64 to 68%), and the bipolar ion concentration ratio is greater than 80 percent (i.e., 84 to 86%).

FIG. 10 provides laboratory tests of a known prior art bipolar ionizer with high-voltage output greater than or equal to 90 percent and bipolar ion concentration ratio less than 80 percent. The row 7-9 tests at input voltages of 20 to 29.3 VAC provide high-voltage output ratios of 90 to 100 percent, bipolar ion concentration ratios of 66 to 77%, and ozone concentrations of 0.08 to 0.27 ppm. The known prior art ozone concentrations are 1.6 to 5.4 times greater than the CARB and US FDA ozone exposure limit of 0.05 ppm. The voltage measurements shown in FIG. 10 are measured at the emitting end of the positive-ion electrode and the negative-ion electrode. Unequal resistors (PER 364 and NER 365 shown in FIG. 5) may be installed between the voltage multipliers and the electrodes for electrical safety. Unequal resistors may impact the voltage measurements of the high-voltage output at the ends of the positive- or negative-ion emitters. The difference in the values of the unequal resistors would not impact the ion generation since the impedance of air is between 1.3 to 3.3 times 10^16 ohms (with ions present) and changes on the order of Mega Ohms (MΩs) between the unequal resistors would be insignificant with respect to the impedance of air (resistance of dry air is infinite with no ions present). The resistance of the unequal resistors may be determined by measuring the high-voltage output from each electrode using a high-voltage measurement circuit shown in FIG. 5 where the RDN is changed for two sets of measurements.

A method of determining an unknown electrode resistor (e.g., PER 364 or NER 365) involves measuring a first voltage V1 with the HMC 363 using the first RDN1 resistor and measuring a second voltage V2 with the HMC 363 using the second RDN2 resistor. The first RDN1 resistor may comprise the positive feedback 100 MΩ resistor 342 and the positive feedback 100 KΩ resistor 344. The second RDN2 resistor may comprise a 200 MΩ resistor plus a 100 KΩ resistor. Equation 3 is used to determine the value of the PER 364 or the NER 365 resistor based on measurements of the first voltage V1 and the second voltage V2.

$$[PER\ 364\ or\ NER\ 365] = [RDN1 - V_r(RDN2)]/[V_r - 1] \qquad Eq.\ 3$$

Where, $V_r = V1/V2$ where the first voltage V1 is measured with the first RDN1 resistor and the second voltage V2 is measured with the second RDN2 resistor, and RDN2=the second RDN2 resistor comprised of a 200 MΩ plus 100KΩ resistor.

Known bipolar ionizers may produce high ozone concentrations greater than the CARB or US FDA limit of 0.050 ppm for 8 to 24 hours. High ozone concentrations may create an unresolved problem regarding human health. The present invention bipolar ionizer provides a solution to the unresolved problem by providing a high-voltage output ratio less than 80 percent, a bipolar ion concentration ratio greater than 80 percent, and zero ozone or nearly zero ozone concentrations over a range of electric signal inputs.

The balanced bipolar ionizer comprises: (1) at least one input terminal for at least one electrical signal input to energize the bipolar ionizer; (2) a signal conditioning element to process the at least one electrical signal input and provide an excitation signal; (3) a step-up transformer to receive the excitation signal from the signal conditioning element and provide a step-up transformer output voltage; (4) a negative voltage multiplier to receive the step-up transformer output voltage and provide a negative high-voltage output to a negative-ion electrode to generate a negative-ion concentration; and (5) a positive voltage multiplier to receive the step-up transformer output voltage and provide a positive high-voltage output to a positive-ion electrode to generate a positive-ion concentration, wherein: the positive voltage multiplier and the negative voltage multiplier provide a high-voltage output ratio less than 80 percent, wherein the high-voltage output ratio is equal to a minimum of an absolute value of a negative high-voltage output and a positive high-voltage output, divided by a maximum of the absolute value of the negative high-voltage output and the positive high-voltage output.

The bipolar ionizer generates a bipolar ion concentration ratio greater than 80 percent, wherein the bipolar ion concentration ratio is equal to a minimum of an absolute value of a negative-ion concentration and a positive-ion concentration, divided by a maximum of the absolute value of the negative-ion concentration and the positive-ion concentration.

The high-voltage output ratio less than 80 percent generates the bipolar ion concentration ratio greater than 80 percent to minimize an ozone concentration to less than ten (10) to fifty (50) parts per billion (ppb) over a range of electrical signal inputs from 20 to 30 Volts Alternating Current (VAC).

The signal conditioning element comprises at least one electrical component selected from the group consisting of: (1) a wire to conduct only one electrical signal input and provide the excitation signal to the step-up transformer, (2) at least one optically isolated triac to conduct the at least one electrical signal input and provide the excitation signal to the step-up transformer, (3) at least one relay to conduct the at least one electrical signal input and provide the excitation signal to the step-up transformer, (4) two diodes and a capacitor to conduct the at least one electrical signal input to a resistor and a Zener diode, a microprocessor, and a first FET to provide the excitation signal to the step-up transformer, and (5) two diodes and a capacitor to conduct the at least one electrical signal input to two resistors, a capacitor, a Zener diode, an oscillator, and the first FET to provide the excitation signal to the step-up transformer.

The signal conditioning element further includes: (1) at least one Resistor Divider Network (RDN) to reduce the positive high-voltage output or the negative high-voltage output to produce at least one high-impedance voltage signal; and (2) at least one active element selected from the group consisting of: an Operational Amplifier (Op Amp), a second FET, and a feedback comparator, wherein the at least one active element converts the at least one high-impedance voltage signal to at least one feedback signal, wherein the at least one feedback signal is used by a microprocessor to vary a frequency and a duty cycle of a digital signal to a first FET to control the excitation signal for the step-up transformer and modulate the frequency and the duty cycle of the step-up transformer output voltage to maintain the high-voltage output ratio less than 80 percent and generate the bipolar ion concentration ratio greater than 80 percent to minimize an ozone concentration over a range of electrical signal inputs from 20 to 30 Volts Alternating Current (VAC) or line voltages from 120 to 480 VAC. The at least one active element maintains a consistent negative DC high-voltage output to a negative-ion electrode to generate a negative-ion concentration and a consistent positive DC high-voltage output to a positive-ion electrode to generate a positive-ion concentration.

The at least one feedback signal is a low-voltage feedback signal or a comparator feedback signal. The positive high-voltage output is +2.5 kV +/−0.6 kV or +1.7 kV+/−0.4 kV. The negative high-voltage output is −1.7 kV+/−0.4 kV or −2.5 kV+/−0.6 kV. the at least one input terminal further includes at least two input terminals to allow the at least one electrical signal input to energize the bipolar ionizer wherein the at least one electrical signal input is selected from at least two electrical signal inputs. The at least one electrical signal input is used to energize the bipolar ionizer to avoid operating the bipolar ionizer continuously which wastes energy and causes dust to accumulate on the negative-ion electrode or the positive-ion electrode when a fan is off which reduces the negative-ion concentration or the positive-ion concentration. The positive voltage multiplier provides at least one more multiplier stage than the negative voltage multiplier or the negative voltage multiplier provides at least one more multiplier stage than the positive voltage multiplier to provide the high-voltage output ratio less than 80 percent and the bipolar ion concentration ratio greater than 80 percent.

The bipolar ionizer with the high-voltage output ratio less than 80 percent and the bipolar ion concentration ratio greater than 80 percent may be installed in at least one application selected from the group consisting of: an inlet or an outlet of an HVAC system blower fan, a forced air unit (FAU), a duct system, a non-enclosed fan, a portable fan, a portable heater, a room air conditioner, a mini-split heat pump, a packaged HVAC system, a packaged terminal air conditioning (PTAC) system, a heat pump, a ceiling fan, a portable air cleaner, a plug-in air cleaner, or air handler to treat an airflow or an air volume for a building, an enclosed environment, an automobile, a boat, a train, an airplane, a space ship, or other indoor environment or transportation system.

The bipolar ionizer includes at least two rare earth magnets attached to a surface of the bipolar ionizer wherein the at least two rare earth magnets are fastened to the surface of the bipolar ionizer in parallel in a consistent North-South orientation or a consistent South-North orientation with respect to a magnetic polarity.

The bipolar ionizer includes a Light Emitting Diode (LED) or a wireless communication module and antenna to provide status information or fault alarm messages.

The bipolar ionizer includes at least one resistor connected between the positive voltage multiplier and the positive-ion electrode, or between the negative voltage multiplier and the negative-ion electrode; and the at least one resistor increases the high-voltage output ratio to greater than or equal to 80 percent, and wherein the high-voltage output ratio is measured at the positive-ion electrode and the negative-ion electrode.

While the invention herein disclosed has been described by means of specific embodiments and applications thereof, numerous modifications and variations could be made thereto by those skilled in the art without departing from the scope of the invention set forth in the claims.

The invention claimed is:

1. An apparatus for a bipolar ionizer, the apparatus comprising:
   at least one input terminal for at least one electrical signal input to energize the bipolar ionizer;
   a signal conditioning element to process the at least one electrical signal input and provide an excitation signal;
   a step-up transformer to receive the excitation signal from the signal conditioning element and provide a step-up transformer output voltage;
   a negative voltage multiplier to receive the step-up transformer output voltage and provide a negative Direct Current (DC) high-voltage output to a negative-ion electrode to generate a negative-ion concentration;
   a positive voltage multiplier to receive the step-up transformer output voltage and provide a positive DC high-voltage output to a positive-ion electrode to generate a positive-ion concentration; and
   wherein the positive voltage multiplier and the negative voltage multiplier provide an unbalanced DC high-voltage output ratio less than 80 percent, wherein the unbalanced DC high-voltage output ratio is equal to a minimum of an absolute value of the negative DC high-voltage output and the positive DC high-voltage output, divided by a maximum of the absolute value of the negative DC high-voltage output and the positive DC high-voltage output;
   wherein the signal conditioning element further includes:
   at least one Resistor Divider Network (RDN) to reduce the positive DC high-voltage output or the negative DC high-voltage output to produce at least one high-impedance voltage signal;
   at least one active element selected from the group consisting of: an Operational Amplifier (Op Amp), a second Field Effect Transistor (FET), and a feedback comparator;
   wherein the at least one active element converts the at least one high-impedance voltage signal to at least one feedback signal, wherein the at least one feedback signal is used by a microprocessor to vary a frequency and a duty cycle of a digital signal to a first FET to control the excitation signal for the step-up transformer and modulate the frequency and the duty cycle of the step-up transformer output voltage to maintain a consistent unbalanced DC high-voltage output ratio and generate a balanced bipolar ion concentration ratio to minimize an ozone concentration over a range of the at least one electrical signal input from 20 to 30 Volts Alternating Current (VAC).

2. The apparatus of claim 1, wherein the bipolar ionizer generates a bipolar ion concentration ratio greater than 80 percent, wherein the bipolar ion concentration ratio is equal to a minimum of an absolute value of the negative-ion concentration and the positive-ion concentration, divided by a maximum of the absolute value of the negative-ion concentration and the positive-ion concentration.

3. The apparatus of claim 2, wherein the unbalanced DC high-voltage output ratio less than 80 percent generates the bipolar ion concentration ratio greater than 80 percent to minimize the ozone concentration to less than fifty (50) parts per billion (ppb) over a range of the at least one electrical signal input from 20 to 30 Volts Alternating Current (VAC).

4. The apparatus of claim 1, wherein the signal conditioning element comprises at least one electrical component selected from the group consisting of:
   at least one optically isolated triac to conduct the at least one electrical signal input and provide the excitation signal to the step-up transformer,
   two diodes and a capacitor to conduct the at least one electrical signal input to a resistor and a Zener diode, the microprocessor, and the first FET to provide the excitation signal to the step-up transformer, and
   two diodes and a capacitor to conduct the at least one electrical signal input to two resistors, a capacitor, a Zener diode, an oscillator, and the first FET to provide the excitation signal to the step-up transformer.

5. The apparatus of claim 1, wherein the at least one feedback signal is a low-voltage feedback signal or a comparator feedback signal.

6. The apparatus of claim 1, wherein the positive DC high-voltage output is +2.5 kV+/−0.6 kV and the negative DC high-voltage output is −1.7 kV+/−0.4 kV.

7. The apparatus of claim 1, wherein the negative DC high-voltage output is −2.5 kV+/−0 0.6 kV and the positive DC high-voltage output is +1.7 kV+/−0 0.4 kV.

8. The apparatus of claim 1, wherein:
   the at least one input terminal further includes at least two input terminals to allow the at least one electrical signal input to energize the bipolar ionizer;
   the at least one electrical signal input is selected from at least two electrical signal inputs; and
   the at least one electrical signal input is used to energize the bipolar ionizer to avoid operating the bipolar ionizer continuously which wastes energy and causes dust to accumulate on the negative-ion electrode or the positive-ion electrode when a fan is off which reduces the negative-ion concentration or the positive-ion concentration.

9. The apparatus of claim 1, wherein the positive voltage multiplier provides at least one more multiplier stage than the negative voltage multiplier or the negative voltage multiplier provides the at least one more multiplier stage than the positive voltage multiplier to provide the unbalanced DC high-voltage output ratio less than 80 percent and a bipolar ion concentration ratio greater than 80 percent.

10. The apparatus of claim 1, wherein the bipolar ionizer further includes a wireless communication module and antenna to provide status information or fault alarm messages.

11. An apparatus for a bipolar ionizer, the apparatus comprising:
    at least one input terminal for at least one electrical signal input to energize the bipolar ionizer;
    a signal conditioning element to process the at least one electrical signal input and provide an excitation signal;
    a step-up transformer to receive the excitation signal from the signal conditioning element and provide a step-up transformer output voltage;
    a negative voltage multiplier to receive the step-up transformer output voltage and provide a negative Direct Current (DC) high-voltage output to a negative-ion electrode to generate a negative-ion concentration;
    a positive voltage multiplier to receive the step-up transformer output voltage and provide a positive DC high-voltage output to a positive-ion electrode to generate a positive-ion concentration; and wherein the excitation signal provided by the signal conditioning is not affected by magnetic fields produced by the position or polarity of magnets attached to a surface of the bipolar ionizer.

12. The apparatus of claim 11, wherein the signal conditioning element comprises at least one electrical component selected from the group consisting of:
   at least one optically isolated triac to conduct the at least one electrical signal input and provide the excitation signal to the step-up transformer,
   two diodes and a capacitor to conduct the at least one electrical signal input to a resistor and a Zener diode, the microprocessor, and the first FET to provide the excitation signal to the step-up transformer, and
   two diodes and a capacitor to conduct the at least one electrical signal input to two resistors, a capacitor, a Zener diode, an oscillator, and the first FET to provide the excitation signal to the step-up transformer.

13. An apparatus for a bipolar ionizer, the apparatus comprising:
   at least one input terminal to receive at least one electrical signal input to energize the bipolar ionizer;
   a signal conditioning element to process the at least one electrical signal input and provide an excitation signal;
   a step-up transformer to receive the excitation signal from the signal conditioning element and provide a step-up transformer output voltage;
   a negative voltage multiplier to receive the step-up transformer output voltage and provide a negative direct current (DC) high-voltage output to a negative-ion electrode to generate a negative-ion concentration; and
   a positive voltage multiplier to receive the step-up transformer output voltage and provide a positive DC high-voltage output to a positive-ion electrode to generate a positive-ion concentration,
   wherein the signal conditioning element further includes:
      at least one Resistor Divider Network (RDN) to reduce the positive DC high-voltage output or the negative DC high-voltage output to produce at least one high-impedance voltage signal; and
      at least one active element to convert the at least one high-impedance voltage signal to at least one feedback signal, wherein the at least one feedback signal is used by a microprocessor to vary a frequency and a duty cycle of a digital signal to a first Field Effect Transistor (FET) to control the excitation signal for the step-up transformer and modulate the frequency and the duty cycle of the step-up transformer output voltage over a range of the at least one electrical signal input from 20 to 30 Volts Alternating Current (VAC) to maintain a consistent negative DC high-voltage output to a negative-ion electrode to generate a negative-ion concentration and a consistent positive DC high-voltage output to a positive-ion electrode to generate a positive-ion concentration.

14. The apparatus of claim 13, wherein the at least one active element is selected from the group consisting of: an Operational Amplifier (Op Amp), a second FET, and a feedback comparator.

15. The apparatus of claim 13, wherein the signal conditioning element comprises at least one electrical component selected from the group consisting of:
   at least one optically isolated triac to conduct the at least one electrical signal input and provide the excitation signal to the step-up transformer,
   two diodes and a capacitor to conduct the at least one electrical signal input to a resistor and a Zener diode, the microprocessor, and the first FET to provide the excitation signal to the step-up transformer, and
   two diodes and a capacitor to conduct the at least one electrical signal input to two resistors, a capacitor, a Zener diode, an oscillator, and the first FET to provide the excitation signal to the step-up transformer.

16. The apparatus of claim 13, wherein the at least one feedback signal is a low-voltage feedback signal or a comparator feedback signal.

17. The apparatus of claim 13, further including at least one of:
   the positive voltage multiplier provides at least one more multiplier stage than the negative voltage multiplier wherein the positive DC high-voltage output is +2.5 kV+/−0.6 kV and the negative DC high-voltage output is −1.7 kV+/−0.4 kV, and
   the negative voltage multiplier provides the at least one more multiplier stage than the positive voltage multiplier wherein the negative DC high-voltage output is −2.5 kV+/−0 0.6 kV and the positive DC high-voltage output is +1.7 kV+/−0.4 kV.

18. The apparatus of claim 13, wherein:
   the at least one input terminal further includes at least two input terminals to allow the at least one electrical signal input to energize the bipolar ionizer:
   the at least one electrical signal input is selected from at least two electrical signal inputs; and
   the at least one electrical signal input is used to energize the bipolar ionizer to avoid operating the bipolar ionizer continuously which wastes energy and causes dust to accumulate on the negative-ion electrode or the positive-ion electrode when a fan is off which reduces the negative-ion concentration or the positive-ion concentration.

19. An apparatus for a bipolar ionizer, the apparatus comprising:
   at least one input terminal for at least one electrical signal input to energize the bipolar ionizer;
   a signal conditioning element to process at least one electrical signal input and provide an excitation signal;
   a step-up transformer to receive the excitation signal and provide a step-up transformer output voltage;
   a negative voltage multiplier to receive the step-up transformer output voltage and provide a negative direct current (DC) high-voltage output to a negative-ion electrode to generate a negative-ion concentration; and
   a positive voltage multiplier to receive the step-up transformer output voltage and provide a positive DC high-voltage output to a positive-ion electrode to generate a positive-ion concentration,
   wherein the signal conditioning element further includes:
      at least one Resistor Divider Network (RDN) to reduce the positive DC high-voltage output or the negative DC high-voltage output to produce at least one high-impedance voltage signal; and
      at least one active element to convert the at least one high-impedance voltage signal to at least one feedback signal used by a microprocessor to vary a frequency and a duty cycle of a digital signal to a first Field Effect Transistor (FET) and control the excitation signal for the step-up transformer to modulate the step-up transformer output voltage over a range of the at least one electrical signal input to maintain a consistent negative DC high-voltage output to a negative-ion electrode to generate a negative-ion concentration and a consistent positive DC highvoltage output to a positive-ion electrode to generate a positive-ion concentration.

20. The apparatus of claim 19, wherein the at least one active element is selected from the group consisting of: an Operational Amplifier (Op Amp), a second FET, and a feedback comparator.

21. The apparatus of claim 19, wherein the signal conditioning element comprises at least one electrical component selected from the group consisting of:
  at least one optically isolated triac to conduct the at least one electrical signal input and provide the excitation signal to the step-up transformer,
  two diodes and a capacitor to conduct the at least one electrical signal input to a resistor and a Zener diode, the microprocessor, and the first FET to provide the excitation signal to the step-up transformer, and
  two diodes and a capacitor to conduct the at least one electrical signal input to two resistors, a capacitor, a Zener diode, an oscillator, and the first FET to provide the excitation signal to the step-up transformer.

22. The apparatus of claim 19, wherein the at least one feedback signal is a low-voltage feedback signal or a comparator feedback signal.

23. The apparatus of claim 19, further including at least one of:
  the positive voltage multiplier provides at least one more multiplier stage than the negative voltage multiplier wherein the positive DC high-voltage output is +2.5 kV+/−0.6 kV and the negative DC high-voltage output is −1.7 kV+/−0.4 kV, and
  the negative voltage multiplier provides the at least one more multiplier stage than the positive voltage multiplier wherein the negative DC high-voltage output is −2.5 kV+/−0 0.6 kV and the positive DC high-voltage output is +1.7 kV+/−0.4 kV.

24. The apparatus of claim 19, wherein:
the at least one input terminal further includes at least two input terminals to allow the at least one electrical signal input to energize the bipolar ionizer:
the at least one electrical signal input is selected from at least two electrical signal inputs; and
the at least one electrical signal input is used to energize the bipolar ionizer to avoid operating the bipolar ionizer continuously which wastes energy and causes dust to accumulate on the negative-ion electrode or the positive-ion electrode when a fan is off which reduces the negative-ion concentration or the positive-ion concentration.

* * * * *